United States Patent [19]

Kofod et al.

[11] Patent Number: 5,968,813
[45] Date of Patent: Oct. 19, 1999

[54] USE OF XYLOGLUCAN ENDOTRANSGLYCOSYLASE (XET)

[75] Inventors: Lene Venke Kofod, Uggerløse; Henrik Lund, Copengagen N, both of Denmark

[73] Assignee: Novo Nordisk A/S, Bagsvaerd, Denmark

[21] Appl. No.: 09/084,596

[22] Filed: May 26, 1998

Related U.S. Application Data

[63] Continuation of application No. PCT/DK96/00538, Dec. 17, 1996.

[30] Foreign Application Priority Data

Dec. 21, 1995 [DK] Denmark ................... 1454/95

[51] Int. Cl.$^6$ ................................................. D06M 16/00
[52] U.S. Cl. ........................... 435/263; 435/97; 435/99; 435/101; 435/200; 435/263; 435/277; 435/278; 536/56; 8/116.1; 8/120
[58] Field of Search ................. 435/97, 99, 101, 435/200, 263, 277, 278; 536/56; 8/116.1, 120

[56] References Cited

U.S. PATENT DOCUMENTS

| | | | |
|---|---|---|---|
| 3,526,048 | 9/1970 | Rowland et al. | 38/144 |
| 4,820,307 | 4/1989 | Welch et al. | 8/120 |
| 5,246,853 | 9/1993 | Clarkson et al. | 435/263 |
| 5,320,645 | 6/1994 | Logue et al. | 8/116.1 |
| 5,443,750 | 8/1995 | Covents et al. | 252/174.12 |
| 5,472,859 | 12/1995 | Brown, Jr. et al. | 435/101 |
| 5,767,364 | 6/1998 | De Silva et al. | 800/205 |

FOREIGN PATENT DOCUMENTS

| | | |
|---|---|---|
| 0 562 836 A1 | 3/1993 | European Pat. Off. . |
| WO 93/05226 | 8/1992 | WIPO . |
| WO 95/13384 | 11/1994 | WIPO . |

OTHER PUBLICATIONS

Fry, Stephen, "Xyloglucan endotransglycosylase, a new wall loosening enzyme activity from plants", Biochemical Journal 282: 821–828, Mar. 1992.

Hawley, Gessner, The Condensed Chemical Dictionary: 166, 262, 749 and 830, 1977.

Hayashi, Takahisha and Deborah Delmer, "Xyloglucan in the cell walls of cottom fiber", Carbohydrate Research 181: 273–277, Oct. 1988.

*Primary Examiner*—Jean C. Witz
*Assistant Examiner*—Angela N. Trafton
*Attorney, Agent, or Firm*—Steve T. Zelson, Esq.; Valeta Gregg, Esq.

[57] ABSTRACT

The invention deals with a process for providing a cellulosic material, such as a fabric or a paper and pulp product, with improved strength and/or shape-retention and/or anti-wrinkling properties, the process comprising contacting, in an aqueous medium, the cellulosic material with a xyloglucan endotransglycosylase (XET).

12 Claims, No Drawings

USE OF XYLOGLUCAN ENDOTRANSGLYCOSYLASE (XET)

CROSS-REFERENCE TO RELATED APPLICATIONS

This application is a continuation application of international application serial no. PCT/DK96/00538 filed Dec. 17, 1996 and claims priority under 35 U.S.C. 119 of Danish application 1454/95 filed Dec. 21, 1995, the contents of which are fully incorporated herein by reference.

FIELD OF INVENTION

The present invention relates to a process for providing a cellulosic material with improved strength and/or shape-retention and/or anti-wrinkling properties.

BACKGROUND ART

Today, virtually all grades of paper, cardboard and the like are produced from aqueous pulp slurry. Typically, the pulp is suspended in water, mixed with various additives and then passed to equipment in which the paper, cardboard etc. is formed, pressed and dried. Irrespective of whether mechanically produced pulp, semi-chemically produced pulp, unbleached chemical pulp or pulp made from recycled fibres (i.e. pulp prepared from recycled paper, rags and the like) is employed, it is often necessary to add various strengthening agents to the pulp in order to obtain an end product having adequate strength properties. In the case of paper and board for use in packaging and the like, the tensile strength and tear strength under dry and wet conditions are of primary importance; moreover, notably in the case of certain grades of cardboard (e.g. so-called unbleached board for the manufacture of corrugated cardboard boxes for packaging, transport and the like), the compression strength of the material is often also an important factor.

Among the strengthening agents used today there are a number of environmentally undesirable substances which it would be desirable to replace by more environmentally acceptable materials. As examples hereof may be mentioned epichlorohydrin, urea-formaldehyde and melamine-formaldehyde.

The industry is also looking for environmental friendly methods for increasing the strength and/or the shape-retention and/or the anti-wrinkling properties of cotton textiles. Today various cross-linking technologies are in use:
DMU technology, in which dimethyl urea and a catalyst are used; this technology has the disadvantage that formaldehyde is released;
DMDHEU technology, in which dimethylol dihydroxyethylene urea and a catalyst are used; this technology has the disadvantage that some formaldehyde is released+the cellulosic material becomes stiff;
BTCA technology, in which butane tetracarboxylic acid and a catalyst are used; this technology has the disadvantage that the formed ester has low durability+the process is expensive.

Thus there is a need in the industry to find a more environmental friendly process for improving the strength and/or shape-retention and/or anti-wrinkling properties of various cellulosic materials; said process should preferably at the same time give a product with a high durability.

SUMMARY OF THE INVENTION

Surprisingly it has been found that it is possible to create an enzymatic process for improving the strength properties of cellulosic materials, so accordingly:

The present invention relates to a process for providing a cellulosic material with improved strength and/or shape-retention and/or anti-wrinkling properties, the process comprising contacting, in an aqueous medium, the cellulosic material with a xyloglucan endotransglycosylase (XET).

DETAILED DESCRIPTION OF THE INVENTION

Cellulosic Materials

According to the present invention a cellulosic material is any material which wholly is or partly made of cellulose.

Examples of such materials are paper and pulp products and cellulosic fabrics.

In the context of the present invention a cellulosic fabric is any cellulose-containing fabric known in the art, such as cotton, viscose, rayon, ramie, linen, Tencel, or mixtures thereof, or mixtures of any of these fibres, or mixtures of any of these fibres together with synthetic fibres or wool such as mixtures of cotton and spandex (stretch-denim), Tencel and wool, viscose and polyester, cotton and polyester, and cotton and wool.

In the context of the present invention a paper or pulp product may be any lignin-containing material, in particular any lignin modified product such as particle boards, fibre boards, or paper.

Xyloglucan Endotransglycosylase (XET)

Xyloglucan endotransglycosylase (XET) is an enzyme known from plants. Stephen C. Fry et al. suggest in *Biochem. J* (1992) 282, p. 821–828 that XET is responsible for cutting and rejoining intermicrofibrillar xyloglucan chains and that XET thus causes the wall-loosening required for plant cell expansion.

XET has been suggested for use in regulating the morphology of a plant, see EP 562 836 p. 2 l. 27–28.

XET is believed to be present in all plants, in particular in all land plants. XET has been extracted from dicotyledons, monocotyledons, in particular graminaceous monocotyledons and liliaceous monocotyledons, and also from a moss and a liverwort, for reference see *Biochem. J* (1992) 282, p. 823.

XET may be obtained from a plant as described in Example 1 (cauliflower) and in Example 5 (green tomatoes), or it may be obtained as described in *Biochem. J* (1992) 282, p. 821–828.

Alternatively, XET may be produced by aerobic cultivation of a transformed host organism, e.g., Aspergillus, in particular *A. oryzae* or *A. niger,* containing the appropriate genetic information from the plant in question. Such transformants can be prepared and cultivated by methods known in the art, e.g., the XET gene may be obtained as disclosed in in EP 562 836, the disclosure of which is hereby incorporated by reference, and the host cells comprising the XET DNA construct may be obtained in the following way:

The host cell is preferably a eukaryotic cell, in particular a fungal cell such as a yeast or filamentous fungal cell or a bacterial cell. In particular, the cell may belong to a species of Trichoderma, preferably *Trichoderma harzianum* or *Trichoderma reesei,* or a species of Aspergillus, most preferably *Aspergillus oryzae* or *Aspergillus niger.* Fungal cells may be transformed by a process involving protoplast formation and transformation of the protoplasts followed by regeneration of the cell wall in a manner known per se. The use of Aspergillus as a host microorganism is described in EP 238 023 (Novo Nordisk A/S), the contents of which are hereby incorporated by reference. The host cell may also be a yeast cell, e.g., a strain of Saccharomyces, in particular *Saccharomyces cerevisiae, Saccharomyces kluyveri* or *Saccharomyces uvarum,* a strain of Schizosaccharomyces sp., such as *Schizosaccharomyces pombe,* a strain of Hansenula sp., Pichia sp., Yarrowia sp., such as *Yarrowia lipolytica,* or Kluyveromyces sp., such as *Kluyveromyces lactis.*

Examples of suitable host bacteria are grampositive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gramnegative bacteria such as *E.coli.* The transformation of the bacteria may, for instance, be effected by protoplast transformation or by using competent cells in a manner known per se.

According to the invention a XET enzyme is preferred which is obtainable from a dicotyledon or a monocotyledon, in particular a dicotyledon selected from the group consisting of cauliflowers, soy beans, tomatoes, potatoes, rapes, sunflowers, cotton, and tobacco, or a monocotyledon selected from the group consisting of wheat, rice, corn and sugar cane.

According to the invention we use the facts that xyloglucan is present in cotton fibers, for reference see *Carbohydrate Research* 181, 1988, p. 273–277, and that xyloglucan is able to make strong hydrogen bonds to cellulose, for reference see *The Plant Journal* 3, 1993, p. 1–30, so by adding the XET enzyme to a cellulosic material we are able to increase the amount of xyloglucan mediated interlinkages between the cellulosic fibres. Hereby we have created an environmental friendly enzymatic process for improving the strength and/or shape-retention and/or anti-wrinkling properties of various cellulosic materials as an alternative to the chemical processes described above.

Determination of XET Activity

XET activity is measured according to Fry et al. in *Biochem.J.* (1992) 282, p. 821–828.

20 $\mu$l of enzyme solution is added 20 $\mu$l of 0.25% xyloglucan (MegaZyme, Australia) in 50 mM sodium acetate buffer pH 6.

8 $\mu$l of tritiated xyloglucan oligomer ($[^3H]XG9$, obtained from C. Fry) is added and the reaction proceeds for 1 h at 30° C. A blank is produced in which the enzyme solution is replaced by buffer. The reaction is stopped by addition of 50 $\mu$l 40% acetic acid. The reaction mixture is applied onto filter paper (Whatman No 3MM) and dried 30 minutes at 60° C. The paper is washed in running deionized water for 1 h and dried 30 minutes at 60° C. The filterpaper is transferred to a scintillation vial, added 5 ml of scintillant (OptiPhase HiSafe, Wallac) and assayed for $^3H$ by scintillation counting.

Industrial Applications

According to the present invention a cellulosic material may get improved strength properties and/or improved shape-retention properties and/or improved anti-wrinkling properties after treatment with the XET enzyme. The XET enzyme has the ability to rearrange and link the xyloglucan molecules which are hydrogen bonded to the cellulosic fibres whereby the above mentioned features may be achieved.

The strength properties may be measured by any method known in the art, e.g., as shown in Examples 3 and 4.

The shape retention properties may be measured by any method known in the art, e.g., as disclosed in the ATCC Test Method 88C-1992, "Retention of Creases in Fabrics after Repeated Home Laundering", which test is designed for evaluating the retention of pressed-in creases in fabrics after repeated home laundering.

The anti-wrinkling properties may be measured by any method known in the art, e.g., as disclosed in the ATCC Test Method 128-1994, "Wrinkle Recovery of Fabrics: Appearance Method", which method is a test for determining the appearance of textile fabrics after induced wrinkling.

In Example 2 of the present patent application we have demonstrated that cotton fabrics contain xyloglucan, and in Example 3 we have shown that it is possible to increase the relative strength of a cotton fabric.

In Example 6 of the present patent application we have shown that a XET treatment may be used for giving a cellulosic material durable press. Unfortunately we have no examples showing the anti-wrinkling properties, but durable press and anti-wrinkling properties are more or less the same.

In order to enhance the effect of the XET enzyme it may in some cases be an advantage to add xyloglucan to the cellulosic material whereby the enzyme may be able to link more cellulosic material together. Example 4 shows the result when xyloglucan is added to the cotton fabric before adding the XET enzyme.

In nature the XET enzyme works in a plant, so the enzyme is able to work in an aqueous environment.

The process of the invention may be carried out in water, or it may be carried out in water in the presence of certain components such as a buffer and/or a wetting agent and/or a stabilizer and/or a polymer and/or an organic component reducing the water activity such as DMSO.

The buffer may suitably be a phosphate, borate, citrate, acetate, adipate, triethanolamine, monoethanolamine, diethanolamine, carbonate (especially alkali metal or alkaline earth metal, in particular sodium or potassium carbonate, or ammonium and HCl salts), diamine, especially diaminoethane, imidazole, Tris or amino acid buffer.

The wetting agent serves to improve the wettability of the cellulosic material. The wetting agent is preferably of a non-ionic surfactant type.

The stabilizer may be an agent stabilizing the XET enzyme.

According to the invention the concentration of XET in the aqueous medium may be 0.01–1000 $\mu$g of enzyme protein per g cellulosic material, preferably 0.1–100 $\mu$g of enzyme protein per g cellulosic material.

It will generally be appropriate to incubate the reaction medium (containing the cellulosic material and the XET enzyme) for a period of at least a few minutes. An incubation time of from 1 minute to 20 hours will generally be suitable, in particular an incubation time of from 30 minutes to 10 hours will often be preferred.

The temperature of the reaction medium in the process of the invention may suitably be in the range of 10–50° C., as appropriate for the XET enzyme in question.

Detergent

In order to improve the strength and/or shape-retention and/or anti-wrinkling properties of the cellulosic fabric the XET enzyme may be an ingredient in a detergent composition or it may be an ingredient in a rinse aid or it may be an ingredient in a softener.

The detergent may be in any convenient form, e.g., powder, granules or liquid.

The detergent normally comprises surfactant which may be anionic, non-ionic, cationic, amphoteric or a mixture of these types. The detergent will usually contain 5–30% anionic surfactant such as linear alkyl benzene sulphonate (LAS), alpha-olefin sulphonate (AOS), alcohol ethoxy sulphate (AES) or soap. It may also contain 3–20% non-ionic surfactant such as nonyl phenol ethoxylate or alcohol ethoxylate.

The detergent may contain 1–40% of a detergent builder such as zeolite, phosphate, phosphonate, citrate, NTA, EDTA or DTPA, or it may be unbuilt (i.e. essentially free of a detergent builder). It may also contain other conventional detergent ingredients, e.g., fabric conditioners, foam boosters, bactericides, optical brighteners and perfumes.

A liquid detergent may be aqueous, typically containing 20–70% water and 0–20% organic solvent.

The pH (measured in aqueous detergent solution) will usually be neutral or alkaline, e.g. 7–10.

The detergent composition will normally comprise other enzymes than the XET enzyme in order to improve cleaning performance and/or fabric care benefits. Such enzymes include proteases, lipases, cutinases, amylases, cellulases, xyloglucanases, peroxidases, and oxidases (e.g. laccases).

The invention is further illustrated in the following examples which are not intended to be in any way limiting to the scope of the invention as claimed.

EXAMPLE 1

Extraction of XET from Cauliflower 250 g of cauliflower is homogenized in 750 ml 50 mM MES, 400 mM NaCl pH 6.2 buffer. 18.75 g PVPP (polyvinyl polypyrrolidone) is added and stirring is continued for 10 minutes. The slurry is filtered and centrifuged 30 minutes at 10000×g. $(NH_4)_2SO_4$ at 80% (516 g/l) is added to the supernatant, and the mixture is stirred until $(NH_4)_2SO_4$ is dissolved. Stirring is continued for further 20 minutes. After centrifugation for 30 minutes at 18000×g the precipitate is suspended in 25 mM MES pH 5.8 and saturated $(NH_4)_2SO_4$ is added 1:1. After 20 minutes the suspension is centrifuged 30 minutes at 18000×g and the precipitate is dissolved in 50 ml 25 mM MES pH 5.8 and is dialysed against 5 liter 25 mM MES pH 5.8 over night. The buffer is changed and dialysis is continued for 1 h. The dialysed sample is applied at 2 ml/min onto a 5 ml HiTrapSP cation exchange column (Pharmacia) calibrated in 25 mM MES pH 5.8 and the column is washed in 2 column volumes of the same buffer. Bound proteins are eluted with 2 volumes of 25 mM MES 500 mM NaCl pH 5.8. Fractions containing XET activity are pooled and applied onto a 4 ml Octhyl Sepharose (Pharmacia) column calibrated in 25 mM MES 35% $(NH_4)_2SO_4$ pH 5.8 at 0.5 ml/min. The column is washed in 2 column volumes of the same buffer and 2 volumes of 25 mM MES 20% $(NH_4)_2SO_4$ pH 5.8. Bound proteins are eluted with 3 volumes of 25 mM MES 40% ethylenglycol pH 5.8. The fractions containing XET activity are pooled into a total volume of 10 ml giving a concentration of XET of about 1 µg/ml, measured by the method described above.

The pooled fractions contained no cellulase activity (measured on AZCL-HE-cellulose from MegaZyme), no xyloglucanase activity (measured on AZCL-xyloglucan from MegaZyme) and no cellobiohydrolase activity (measured as the formation of reducing sugar from acid swollen Avicel).

EXAMPLE 2

XET Mediated Incorporation of [$^3$HXG9] to Cotton Fabric 0.05 g of cotton fabric is added 600 µl 50 mM sodium acetate pH 6.0, 16 µl [$^3$HXG9] and 40 µl of cauliflower XET solution obtained as described in Example 1.

Incubation takes place over night at 30° C. The cotton fabric is washed 1 hour in running water and dried 30 minutes at 65° C. The piece of fabric is transferred to a scintillation vial and assayed for $^3$H as described. Two blanks are produced, one where the XET solution is replaced by buffer and one where the XET solution has been inactivated by boiling for 20 minutes. The counts per minute (CPM) are seen in Table 1:

TABLE 1

| Incorporation of xyloglucan oligomer to cotton fabric | |
|---|---|
| | CPM |
| No XET | 23 |
| Inactivated XET | 24 |
| XET | 149 |

The results in Table 1 show that cotton fabric contain xyloglucan to which other xyloglucan molecules can be attached by the action of XET.

EXAMPLE 3

Measurements of Strength of Fabric

The following example illustrates the ability of xyloglucan endotransglycosylase (XET) to impart improved strength properties into cellulosic fabrics. Trials were made with XET derived from cauliflower as described in Example 1.

Swatches of woven 100% cotton (4 pieces of 1.5 cm×4.0 cm) were incubated with approximately 50 ng XET for three hours in 40 ml 50 mM Tris-buffer pH 5.8 at 25° C. For comparison a blank trial was made without the addition of XET.

Following the incubation, the swatches were carefully rinsed in deionized water and cut into a size of 1.0 cm×3.0 cm in order to avoid measuring on partically untwisted yarn-ends.

After the rinse, the swatches were kept in deionized water for 15 minutes prior to wet tensile strength measurement.

The tensile strength of the swatches was measured (in the length direction) with an INSTRON Model 5564 with a distance between the clamps of 2.5 cm.

Results are listed in Table 2 below:

| Sample | Relative wet tensile strength, average |
|---|---|
| Blank (only buffer) | 100% |
| XET | 107.5% |

EXAMPLE 4

Incubating Cellulosic Fabrics with Xyloglucan

The following example illustrates that incubating cellulosic fabrics with xyloglucan followed by treatment with xyloglucan endotransglycosylase (XET) can serve as an alternative route to impart improved strength properties into cellulosic fabrics.

Trials were made with XET derived from cauliflower as described in Example 1.

Swatches of woven 100% cotton (8 pieces of 1.5 cm×4.0 cm) were soaked for 15 minutes in 100 ml deionized water containing 0.50 g/l xyloglucan obtained from tamarind seed (xyloglucan (Amyloid), Lot TXG90901, obtained from MegaZyme, Australia), 25° C. The swatches were removed from the xyloglucan solution. Still wet, four of the swatches were then incubated with approximately 50 ng XET for three hours in 40 ml 50 mM Tris-buffer pH 5.8 at 25° C., while the last four swatches were incubated in 40 ml Tris-buffer pH 5.8 without any XET present (BLANK).

Following the incubation, the swatches were carefully rinsed in deionized water and cut into a size of 1.0 cm×3.0 cm in order to avoid measuring on partially untwisted yarn-ends. After the rinse, the swatches were kept in deionized water for 15 minutes prior to wet tensile strength measuremnt. The wet tensile strength of the swatches was measured (in the length direction) with an INSTRON Model 5564 with a distance between the clamps of 2.5 cm.

Result are listed in Table 3 below:

| Sample | Relative wet tensile strength, average |
| --- | --- |
| Blank (only buffer) | 100% |
| XET | 115.9% |

EXAMPLE 5

Extraction of XET from Green Tomatoes 10 kg of green tomatoes were cut in halves and the kernels were removed before immediate freezing in liquid nitrogen. The resulting 7.2 kg of frozen tomatoes were suspended in 10.8 kg 0.1M sodium phosphate buffer pH 7.2 with 1% Polyvinyl polypyrrolidone. The suspension was homogenised at 0° C. in a mill with cooling. The paste was stirred for 1 h at 0° C. before filtering which resulted in 13.7 kg of filtrate. The temperature was kept below 3° C. 8.3 kg of amonium sulphate was added and the solution was stirred for 45 min at 0° C. The precipitated material was recovered by centrifugation. The sediment was dissolved in 2 liter of 0.2M sodium acetate pH 5.7 giving a total of 7.4 liter. Then 1.2 liter of saturated amoniun sulphate solution was added. After stirring for 15 min at 3° C. the precipitated material was recovered by centrifugation. The sediment was dissolved in 500 ml 0.2M sodium acetate buffer pH 5.7 and dialysed against the same buffer over night at 3° C. The dialysis tube was D 0655 from Sigma with a 12000 Da cut off. The content of the dialysis tube was centrifuged, which yielded 600 ml of XET solution.

XET activity was confirmed by the XET assay and the absence of cellulase and xyloglucanase activity was confirmed by testing at pH 6.0 on AZCL-HE-cellulose and AZCL-xyloglucan from Megazyme, Australia.

The tomato XET solution was used for testing of durable press finishing effect on cotton fabric (Example 6) and for testing strengthening of paper (Example 7).

EXAMPLE 6

Durable Press with XET

Four pieces of white woven fabric (6 cm×140 cm) were desized with a 0.05% solution of Termamyl 300 L (produced by Novo Nordisk) for 10 minutes at 60° C. The fabric was rinsed in water for 10 minutes. The fabric was transferred to four trays with destilled water, and in two of these were additionally 0.1% xyloglucan (Tamarind gum, Lot TXG90901, from MegaZyme, Australia). After soaking for one hour the swatches were removed from the solution, and rinsed in water for 10 minutes.

Each swatch was folded 6 times and put into a tray with 0.2M sodium acetate buffer pH 5.5. In two of the trays we added 10 ml of XET containing solution from green tomatoes (see Example 5). Volume was adjusted to a total of 150 ml with the buffer. A heavy weight (2.5 kg) was put on top of each folded swatch in such a way that there was an even pressure on the folded fabric. After 24 hours incubation in a dark room at room temperature (app. 25° C.) the fabric was rinsed with water in a washing machine at the short cycle 40° C. programme. The swatches were dried flat until next morning. The fabric was visually evaluated for crease marks. It was very clear that the XET treatment could be used for giving durable press, as only the XET treated swatches had retained the press folds:

| XET | Xyloglucan | Visual observation |
| --- | --- | --- |
| No | No | No crease marks |
| Yes | No | Clear crease marks at folds |
| No | Yes | Maybe some crease marks at folds |
| Yes | Yes | Clear crease marks at folds |

Conclusion: XET treated fabric had crease marks that could easily be observed visually. Addition of xyloglucan was not necessary for the crease marks, but addition of xyloglucan gave itself a tendency towards crease marks.

EXAMPLE 7

Use of XET for Strengthening Paper

Hand sheets of pine TMP pulp (130 g/m$^2$) were made in a PFI sheet mould. The sheets were then pressed in a sheet press for 5 minutes at a pressure of 400 kPa. After pressing, the wet sheets were placed on a net and immersed in different solutions. In all cases the sheets were immersed for 30 minutes, and the temperature of the solution was 25° C.

The different solutions were as follows:

Control: Immersed in water

Xyloglucan endotransglycosylase: immersed in a solution of XET (6.67% solution of the enzyme stock solution from Example 5. Each sheet takes up approx. 1.8 g of enzyme solution, which corresponds to 0.45 g enzyme solution per gram of fibre dry matter.)

After immersion, the sheets were pressed in the sheet press for 15 minutes at a pressure of 400 kPa. After pressing the sheets were dried overnight at room temperature.

Thickness and tensile index for the sheets were measured according to the SCAN standards SCAN-P7 and SCAN-P16.

From the experiments it is seen that the addition of XET increases the tensile strength of the sheet:

| Treatment | Tensile strength (kNm/kg) |
| --- | --- |
| Control | 4.12–4.57 |
| XET | 8.95–8.40. |

We claim:

1. A process for providing a cellulosic material with improved strength and/or shape-retention and/or anti-wrinkling properties, the process comprising contacting, in an aqueous medium, the cellulosic material with an effective amount of a xyloglucan endotransglycosylase (XET).

2. The process of claim 1, wherein the cellulosic material is a cellulosic fabric or a paper and pulp product.

3. The process of claim 1, wherein the XET enzyme is obtainable from a plant.

4. The process of claim 3, wherein the plant is dicotyledon or a monocotyledon.

5. The process of claim 4, wherein the dicotyledon is selected from the group consisting of cauliflowers, soy beans, tomatoes, potatoes, rapes, sunflowers, cotton, and tobacco.

6. The process of claim 4, wherein the monocotyledon is selected from the group consisting of wheat, rice, corn, and sugar cane.

7. The process of claim 1, wherein the XET enzyme is produced by aerobic cultivation of a host organism transformed with DNA encoding the XET enzyme.

8. The process of claim 1, wherein the concentration of the XET enzyme corresponds to 0.01–1000 $\mu$g of enzyme protein per g of cellulosic material.

9. The process of claim 1, wherein the aqueous medium additionally contains xyloglucan.

10. A cellulosic material produced by the process of treating in an aqueous medium cellulosic material with an effective amount of a xyloglucan endotransglycosylase (XET), wherein the treated material is characterized as having improved strength, shape-rentention, and/or anti-wrinkling properties, wherein the improved properties result from reaarranging and linking of xyloglucan molecules.

11. A detergent composition comprising a xyloglucan endotransglycosylase (XET) enzyme and a surfactant.

12. The process of claim 8, wherein the concentration of XET corresponds to 0.1–100 $\mu$g of enzyme protein per g of cellulosic material.

* * * * *